United States Patent [19]

Buckman

[11] 4,234,511

[45] Nov. 18, 1980

[54] DIALKYLAMINO-N,N-BIS(PHOS-PHONOALKYLENE)ALKYLAMINES AND USE IN AQUEOUS SYSTEMS AS PRECIPITATION AND CORROSION INHIBITORS

[75] Inventor: John D. Buckman, Memphis, Tenn.

[73] Assignee: Buckman Laboratories, Inc., Memphis, Tenn.

[21] Appl. No.: 61,168

[22] Filed: Jul. 26, 1979

[51] Int. Cl.$^3$ .......................... C07F 9/38; C09K 3/00; C23F 11/10

[52] U.S. Cl. .................. 260/502.5; 252/180; 252/389 R; 210/700; 260/945; 564/292

[58] Field of Search ....................... 260/502.5

[56] References Cited

U.S. PATENT DOCUMENTS

| | | | |
|---|---|---|---|
| 2,599,807 | 6/1952 | Bersworth | 260/502.5 |
| 2,841,611 | 7/1958 | Bersworth | 260/502.5 |
| 2,964,549 | 12/1960 | Ramsey et al. | 260/502.5 |
| 3,160,632 | 12/1964 | Toy et al. | 260/502.5 |
| 3,288,846 | 11/1966 | Irani et al. | 260/502.5 |
| 4,054,598 | 10/1977 | Blum et al. | 260/502.5 |
| 4,064,164 | 12/1977 | Blum et al. | 260/502.5 |

*Primary Examiner*—Joseph E. Evans
*Attorney, Agent, or Firm*—Floyd Trimble

[57] ABSTRACT

Dialkylamino-N,N-bis(phosphonoalkylene)alkylamines, salts, and specifically the hydrochlorides thereof prepared by reacting an unsymmetrical dimethylaminoalkylamine hydrochloride with phosphorous acid and an aldehyde are useful in various industrial processes including acting as corrosion and scale inhibitors in aqueous systems wherein such corrosion and scale problems exist. Quaternized dialkylamino-N,N-bis(phosphonoalkylene)alkylamines suitable for the same uses are prepared by the treatment of an aqueous solution of a dialkylamine-N,N-bis(phosphonoalkylene)alkylamine with an epoxide or a halohydrin.

5 Claims, No Drawings

DIALKYLAMINO-N,N-BIS(PHOSPHONOALKYLENE)ALKYLAMINES AND USE IN AQUEOUS SYSTEMS AS PRECIPITATION AND CORROSION INHIBITORS

BACKGROUND OF THE INVENTION

Cooling water systems are subject to formation of scale deposits. Scaling can occur when the concentration of a dissolved substance in a cooling water becomes greater than its solubility in the water. It can especially be a problem with a substance that has an inverse solubility curve; that is, a material whose solubility decreases as the temperature increases. Since water temperatures at or near heat-transfer surfaces are greater than temperatures in the bulk of the system, the solubility of such materials is less in these regions. Consequently, they tend to precipitate and form scales that reduce heat-transfer efficiency.

One principal scale-forming material encountered in cooling water systems is calcium carbonate formed by the decomposition of calcium bicarbonate. This compound not only has an inverse solubility curve, but its solubility is much lower in most typical cooling waters than almost all other potential scale-formers that might be present in these waters. Of course, calcium carbonate is soluble in acidic solutions, and as the pH of a cooling water is lowered, scale generally becomes less of a problem. However, most cooling waters are kept on the alkaline side to reduce corrosion, and thus calcium carbonate scaling remains as a potential problem. Calcium sulfate, calcium phosphate, barium sulfate, and ferric hydroxide can also cause scale. Thus, to be a broadly useful composition, a scale control product must be capable of controlling different scale types.

It is well known that the operation of commercial and industrial cooling systems is adversely affected by a number of different factors. Of these adverse factors, corrosion of metallic parts coming into contact with the water is probably one of the most serious. If not controlled, corrosion causes the rapid deterioration of the metallic materials of construction used in cooling towers and associated equipment such as pumps, pipelines and valves, causing major losses in overall efficiency of the cooling systems. While control of bleedoff, pH, and other operating variables is helpful in reducing corrosion, chemical treatment of the water is generally the most effective and economical means of minimizing this problem, particularly where conservation of water by means of recycling is necessary or desired.

Waterside problems encountered in boilers and steam systems include the formation of scale and other deposits, corrosion, and foam. Scale and other deposits on heat-transfer surfaces can cause loss of the thermal efficiency of the boiler and can make the temperatures of the boiler metal increase. Under scaling conditions, temperatures may go high enough to lead to failure of the metal due to overheating. Corrosion in boilers and steam systems also causes failure of boiler metal and damage to steam and condensate lines.

The principal source of deposits in boilers is dissolved mineral matter in the boiler feedwater. The term "scale" is generally used for deposits that adhere to boiler surfaces exposed to the water, while nonadherent deposits are called "sludge" or "mud." Scale causes more difficulty because the sludge can be purged from the system with the blowdown or can be easily washed out, but scale can normally only be removed by mechanical or chemical cleaning of the boiler.

In natural, untreated water, the main sources of scale and sludge are calcium carbonate, calcium sulfate, magnesium hydroxide, and silica. The most common type of scale in boilers is probably calcium carbonate, but the most troublesome is usually calcium sulfate. The latter causes more difficulties because its solubility decreases more rapidly with increasing temperatures than does that of other substances, and the scale it forms is hard, dense, and difficult to remove. On the other hand, calcium carbonate tends to form sludge more than scale, and the calcium carbonate scales that do form are generally softer and easier to remove. Magnesium hydroxide precipitates are not very adherent and tend to form sludges rather than scales.

It is often desirable in today's technology to prevent precipitation of alkaline earth salts or of iron salts from water or aqueous solutions. For this purpose inorganic and organic sequestering agents have previously been proposed and utilized. For instance, the organic compounds nitrilo triacetic acid or ethylenediamine tetraacetic acid have been used. Likewise polymeric phosphates have also been used as sequestering agents. The latter have the advantage that they can prevent precipitation even if applied in less than a stoichiometric amount. The disadvantages of the polymeric phosphates, however, are that they lose effectiveness at elevated temperatures and that they readily hydrolyze, particularly in the acidic pH range. For reasons related to sewage disposal, additional problems may develop in the use of phosphates. It has already been proposed to use organic phosphonic acids, such as non-substituted aminotrimethylene phosphonic acid, for this purpose, but it has been found that corrosion problems occur therefrom.

Aminoalkylenephosphonic acids and their metal and ammonium salts are well known compounds and recognized metal complexing agents. The quaternization of such compounds in an aqueous solution has not heretofore been achieved. Under normal reaction conditions, there is apparent protonation (or zwitter ion formation) of the free electrons on the nitrogen atoms in the molecule. Conditions which are sufficiently alkaline to remove said proton tend to destroy the alkylating agent faster than it can react in the desired fashion.

OBJECTS OF THE INVENTION

It is an object of the present invention to provide novel dialkylamino-N,N-bis(phosphonoalkylene)amine hydrochlorides having valuable properties.

It is another object of our invention to provide the alkali metal and ammonium salts of such compounds.

It is a further object of our invention to provide a process for inhibiting the precipitation of insoluble salts from aqueous solutions comprising adding to an aqueous solution containing a precipitable salt, a composition selected from the group consisting of (a) a dialkylamino-N,N-bis(phosphonoalkylene)alkylamine, (b) hydrochloride thereof, (c) alkali metal salt or ammonium salt thereof, and (d) quaternary ammonium derivatives thereof.

It is yet another object of this invention to provide a process for inhibiting the corrosion of metals in contact with an aqueous system comprising adding thereto a composition selected from the group consisting of (a) a dialkylamino-N,N-bis(phosphonoalkylene)alkylamine, (b) hydrochloride thereof, (c) alkali metal salt or ammonium salt thereof, and (d) quaternary ammonium derivatives thereof.

A further object of this invention is to provide a composition that is compatible with other water treatment agents to achieve maximum efficiency in the control of both scale and corrosion.

These and other objects and advantages will become apparent as the description proceeds.

SUMMARY OF THE INVENTION

According to the present invention it has been found that certain dialkylamino-N,N-bis(phosphonoalkylene)alkylamines and their alkali metal or ammonium salts, corresponding to the formula

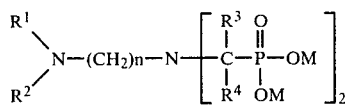

wherein $R^1$ and $R^2$ represent an alkyl group containing 1 to 4 carbon atoms, $R^3$ and $R^4$ represent hydrogen or an alkyl group containing 1 to 4 carbon atoms, M represents hydrogen, an alkali metal or ammonium, and n is an integer varying from 2 to 6 and further characterized in that when M is hydrogen the composition is a hydrohalide salt and their quaternary ammonium salts formed by reacting the alkali metal salts thereof with halohydrins or epoxides. These compounds are precipitation inhibitors and corrosion inhibitors when used in stoichiometric and substiochiometric amounts, including that phenomenon known in the art as the 'threshold effect.'

DESCRIPTION OF PREFERRED EMBODIMENTS

The dialkylamino-N,N-bis(phosphonoalkylene)alkylamine hydrochloride of the present invention may be prepared by reacting an unsymmetrical dimethylaminoalkylamine hydrochloride with phosphorous acid and an aldehyde in the proper molecular proportions. Variations in specific structure of the compounds are possible through variations in the value of n and in the structure of $R^1$, $R^2$, $R^3$, and $R^4$.

The preferred dialkylamino-N,N-bis(phosphonoalkylene)alkylamine hydrochloride is

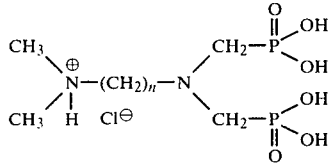

where n is 3.

Derivatives of dialkylamino-N,N-bis(phosphonoalkylene)alkylamines may be prepared by reacting their alkali metal salts with a halohydrin or an epoxide in the proper molecular proportions as described in the examples. Variations in specific structure of these compounds are possible through variations in the value of n and in the structure of $R^1$, $R^2$, $R^3$, and $R^4$. These compounds were identified by titration values and by their characteristic NMR and infrared bands as quaternized dialkylamino-N,N-bis(phosphonoalkylene)alkylamines.

The amines used in the preparation of the compositions of this invention contain on primary amine and at least one secondary or tertiary amine such as unsym. N,N-dimethylethylenediamine and unsym. N,N-dimethylaminopropylamine.

Typical examples of suitable aldehydes are formaldehyde, acetaldehyde, propionaldehyde and butyraldehyde.

Orthophosphorous acid is readily available commercially. It can be utilized in the process of the present invention either as the acid or in the form of its salts, such as its mono- or di-alkali metal salts. When orthophosphorous acid is utilized in the salt form, usually a small amount of a supplementary acid should be utilized in order to effectively convert the salt form into the more reactive orthophosphorous acid.

The epoxides and chlorohydrins that can be used for the preparation of the quaternary ammonium salts of this invention are ethylene oxide, propylene oxide, epichlorohydrin, 3-chloro-1,2-propoanediol (α-chlorohydrin), low mmolecular weight hydroxylated ionene polymers with halogen end groups, etc.

The aminoalkylenephosphonic acids and salts of our invention may be utilized as solids, as solutions in water or in polar organic solvents or in combinations of water and organic solvents. When used for scale inhibition, the aminoalkylenephosphonates may be used alone or in combination with other scale inhibitors. Examples of these would be alkali metal phosphates, alkali metal polyphosphates, alkali metal tripolyphosphates, alkali metal pyrophosphates, organic water soluble polymers containing a linear hydrocarbon structure with side chain carboxylic acid groups exemplified by the structure:

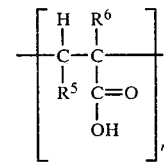

where $R^5$ is hydrogen or —COOH and $R^6$ is hydrogen or methyl. These polymers may be obtained from acrylic acid or methacrylic acid. Polymers of maleic anhydride can be prepared and the anhydride group hydrolyzed with water to provide carboxylic acid groups. Acrylonitrile and acrylamide polymers may also be hydrolyzed with hot alkaline solutions to eliminate ammonia and form carboxylic acid salts. Copolymers of all of the monomers listed may also be prepared and these copolymers may be hydrolyzed to the carboxylic acid groups if the anhydride, amide, or nitrile groups are contained in the copolymer. These polymers may be utilized as the free acid or as water soluble salts such as the alkali metal and alkaline earth metal salts. The polymers used in this invention are either commercially available or methods for their preparation are well known in the art. In addition, poly(acrylamide) of low molecular weight may be combined with the phosphonates of this invention.

The aminoalkylenephosphonic acids of this invention can be formulated with such polymers as poly(acrylic acid) with both ingredients used as the free acids. This is advantageous when the products are used in closed systems such as recirculated cooling water systems. In such systems, the evaporation of water increases the solids content of the water and increases the pH at the same time, particularly if alkaline scale inhibitors are being added. The cycles of concentration in those systems can be markedly increased if the additive has an acid pH.

The aminoalkylenephosphonates of this invention act as corrosion inhibitors for mild steel. Formulations of these phosphonates with corrosion inhibitors such as water soluble zinc salts will provide both scale inhibition and synergistic corrosion protection. Combinations of the phosphonates with 2-mercaptobenzothiazole, benzotriazole, and tolyltriazole will give good corrosion inhibition on both copper alloys and steel. Additional compounds which have been used as corrosion inhibitors and which can be used in combination with the aminoalkylene-phosphonates of this invention include phosphates, polyphosphates, organic water soluble polymers, silicates, dithiocarbamates, nitrites, oxazoles, imidazoles, lignins, lignosulfonates, tannins, phosphoric acid esters, boric acid esters, alkali metal salts of inorganic molybdenum and chromium compounds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

The amount and manner of use of the scale, sludge, and corrosion control compositions of our invention are dependent on the nature of the problems caused by scale and sludge in the particular system. In general, suitable quantities of the compounds of this invention vary from 0.5 to 500 parts per million parts by weight of water. Preferred quantities vary from 1.0 to 200 parts per million parts of water. It is understood, of course, that larger quantities may be used, but such is generally not desirable because coats are increased without commensurate additional beneficial results.

In order to disclose the nature of the invention still more clearly, the following illustrative examples will be given. It is understood, however, that the invention is not to be limited to the specific conditions or details set forth in these examples, except insofar as such limitations are specified in the appended claims.

EXAMPLE 1

3-(N,N-Dimethylamino)-N',N'-bis(phosphonomethyl)-propylamine Hydrochloride

To 511.0 g (5.0 moles) of 3-dimethylaminopropylamine 985.5 g of concentrated hydrochloric acid (10.0 moles) was added slowly at such a rate as to keep the temperature below 50° C. during the addition. When the introduction of the hydrochloric acid was completed, 1171.4 g (10.0 moles) of phosphorous acid was added rapidly and the stirred mixture was heated to 60° to 65° C. At this point 892.8 g (11.0 moles) of 37 percent aqueous formaldehyde was slowly introduced. The reaction was exothermic. After the introduction of the formaldehyde the mixture was refluxed for two hours. An aliquot of the resulting mixture was triturated under ethanol to yield a white powdery material that was further purified by recrystallization from hot ethyl alcohol. The compound was identified by its characteristic infrared spectrum and by elemental analysis as 3-(N,N-dimethylamino)-N',N'-bis(phosphonomethyl)propylamine hydrochloride. Analysis calcd for $C_7H_{21}ClN_2O_6P_2$: C, 25.73 percent; H, 6.48 percent; N 8.57 percent; and P, 18.96 percent. Found: C, 25.85 percent; H, 6.76 percent; N, 8.57 percent; and P, 19.02 percent. Melting range 165°–175° C.

EXAMPLE 2

Reaction of 3-(N,N-Dimethylamino)-N',N'-bis(phosphonomethyl)-propylamine with Epichlorohydrin To a solution of 16.3 g (0.05 mole) of 3-(N,N-dimethylamino)-N',N'-bis(phosphonomethyl)propylamine hydrochloride in 30.0 g of water, 12.0 g of 50 percent sodium hydroxide solution was added at such a rate as to keep the temperature of the stirred mixture between 40° and 50° C. To the resulting sodium salt solution, 4.6 g (0.05 mole) of epichlorohydrin wasa added and the mixture was stirred at the reflux temperature for two hours. The resulting solution was tested without purification. An aliquot of the solution was triturated under ethanol to yield a white hygroscopic solid that was further purified by recrystallization from hot ethyl alcohol and dried in a vacuum desiccator over $P_2O_5$. The compound was characterized by its distinguishing infrared and NMR bands and by titration as quaternary ammonium salt, but that exact structure was not precisely determined.

EXAMPLE 3

Reaction of Two Moles of 3-(N,N-Dimethylamino)-N',N'-bis(phosphonomethyl)-propylamine with One Mole of Epichlorohydrin Into a 1-liter, 3-neck, round-bottom flask equipped with a stirrer, thermometer and reflux condenser was charged 178.0 g of a 45.88 percent aqueous solution of 3-(N,N-dimethylamino)-N',N'-bis(phosphonomethyl)-propylamine hydrochloride (0.25 mole). The pH of this solution was adjusted to 7.5–7.6 by the addition of 50 percent aqueous sodium hydroxide solution at such a rate as to keep the temperature of the stirred mixture below 50° C. (Approximately 105.0 g of 50 percent aqueous sodium hydroxide solution was needed.) To the resulting sodium salt solution 23.2 g (0.25 mole) of epichlorohydrin was added the mixture was refluxed for two hours. At this point an aqueous solution of 3-(N,N-dimethylamino)-N',N'-bis(phosphonomethyl)propylamine trisodium salt [prepared by adjusting the pH of 178.0 g of a 45.88 percent aqueous solution of 3-(N,N-dimethylamino)-N',N'-bis(phosphonomethyl)propylamine hydrochloride to 9.4–9.6] was added and the resulting solution was refluxed for an additional two hours. The product obtained was tested without purification. An aliquot of the solution was triturated under ethanol to yield a white hygroscopic solid that was further purified by recrystallization from hot ethyl alcohol and dried in a vacuum desiccator over $P_2O_5$. The compound was characterized by its distinguishing infrared and NMR bands and by titration as a bis quaternary ammonium salt, but the structure was not precisely determined.

EXAMPLE 4

Preparation of N,N,N',N'-Tetramethyl-N,N'-bis(3-chloro-2-hydroxypropyl)ethylenediammonium Dichloride One hundred eighty-seven and eight tenths grams (1.0 mole) of a 61.87 percent aqueous solution of tetramethylethylenediamine was placed into a 1-liter, four-neck, round-bottom flask equipped with a reflux condenser, mechanical stirrer, thermometer and a dropping funnel and, while stirring, 197.1 g (2.0 moles) of concentrated hydrochloric acid was introduced at such a rate as to keep the temperature between 40° and 50° C. When all the hydrochloric acid was introduced 185.0 g (2.0 moles) of epichlorohydrin was added to the tetramethylethylenediamine dihydrochloride solution, again taking care that the temperature did not exceed 50° C. When this addition was completed, the temperature of the stirred mixture was raised to between 65° and 71° C. where it was kept for thirty minutes. The resulting solution containing 65.66 percent of the diquaternary ammonium salt was used in subsequent reactions.

EXAMPLE 5

Reaction of 3-(N,N-Dimethylamino)-N',N'-bis(phosphonomethyl)propylamine with N,N,N',N'-Tetramethyl-N,N'-bis(3-chloro-2-hydroxypropyl)ethylenediammonium Dichloride Into a 1000-ml, four-neck, round-bottom flask equipped with a mechanical stirrer, reflux condenser, thermometer and a dropping funnel was placed 356.0 g of 45.88 percent aqueous 3-(N,N-dimethylamino)-N',N'-bis(phosphonomethyl)propylamine hydrochloride solution (0.5 mole) followed by enough 50 percent aqueous sodium hydroxide solution to adjust the pH of the mixture to 7.5-7.6. After the pH adjustment was made, 285.0 g (0.5 mole) of the solution described in Example 4 was introduced and the resulting mixture was stirred and refluxed for two hours. The product obtained was tested without purification or isolation.

EXAMPLE 6

Reaction of Two Moles of 3-(N,N-Dimethylamino)-N',N'-bis(phosphonomethyl)propylamine with One Mole of N,N,N',N'-Tetramethyl-N,N'-bis(3-chloro-2-hydroxypropyl)ethylenediammonium Dichloride Into a 1000-ml, four-neck, round-bottom flask equipped with a mechanical stirrer, reflux condenser, thermometer and a dropping funnel was placed 356.0 g of a 45.88 percent aqueous solution of 3-(N,N-dimethylamino)-N',N'-bis(phosphonomethyl)propylamine hydrochloride (0.5 mole) followed by enough 50 percent aqueous sodium hydroxide solution to raise the pH of the mixture to 7.5-7.6. After the pH was adjusted, 258.0 g (0.5 mole) of the solution of Example 4 was introduced slowly and the resulting mixture was stirred at the reflux temperature for two hours. At this point an aqueous solution of 3-(N,N-dimethylamino)-N',N'-bis(phosphonomethyl)propylamine trisodium salt [prepared by adjusting the pH of 356.0 g of a 45.88 percent aqueous solution of 3-(N,N-dimethylamino)-N',N'-bis(phosphonomethyl)propylamine hydrochloride to 9.4-9.6] was added and the resulting solution was refluxed for an additional two hours. The product obtained was tested without purification.

EXAMPLE 7

2-Dimethylamino-N',N'-bis(phosphonomethyl)ethylamine Hydrochloride

Example 1 was repeated in every detail except that 441.0 g (5.0 moles) of N,N-dimethylethylenediamine was substituted for N,N-dimethylaminopropylamine. The resulting solution was used for testing in this form without isolation or purification.

EXAMPLE 8

Product of the Reaction of N,N-Dimethylcocoamine with Epichlorohydrin and 3-(N,N-Dimethylamino)-N',N'-bis(phosphonomethyl)propylamine Disodium Salt N,N-Dimethylcocoamine hydrochloride was prepared by treating 59.8 g (0.25 mole) of the free amine (supplied by Humko Sheffield Chemical Company as Kemamine T-6502D) with 24.7 g (0.25 mole) of concentrated hydrochloric acid while keeping the temperature below 50° C. Epichlorohydrin (23.1 g, 0.25 mole) was added slowly between 50° and 60° C. The temperature was raised and the mixture heated at 100°-105° C. for two hours. The resulting mixture was cooled to 50° C. and a solution of 3-(N,N-dimethylamino)-N',N'-bis(phosphonomethyl)propylamine trisodium salt [prepared by adjusting the pH of 178.0 g of a 45.88 percent aqueous solution of 3-(N,N-dimethylamino)-N',N'-bis(phosphonomethyl)propylamine hydrochloride to 9.4-9.6] was added. The resulting mixture was again treated at 100°-105° C. for two hours. A grease-like product was obtained. This product was tested in this form without further purification or isolation of the active ingredient.

EXAMPLE 9

Preparation of Poly[2-hydroxyethylene(dimethyliminio)ethylene(dimethyliminio)]methylene Dichloride Into a 2-liter, three-neck, round-bottom flask equipped with a mechanical stirrer, reflux condenser and a thermometer was placed 854.8 g of a 65.66 percent aqueous solution (1.5 moles) of the diquaternary ammonium salt of Example 4 and 187.8 g of a 61.87 percent aqueous solution of tetramethylethylenediamine. The stirred mixture was refluxed for one hour and the resulting solution which contained 63.49 percent of the desired low molecular weight ionene polymer was used in reactions is this form.

EXAMPLE 10

Reaction of Two Moles of 3-(N,N-Dimethylamino)-N',N'-bis(phosphonomethyl)propylamine with One Mole of Poly[2-hydroxyethylene(dimethyliminio)ethylene(dimethyliminio)]methylene Dichloride Into a 1-liter, three-neck, round-bottom flask equipped with a mechanical stirrer, reflux condenser and a thermometer was charged 356.0 g of a 45.88 percent aqueous solution of 3-(N,N-dimethylamino)-N',N'-bis(phosphonomethyl)propylamine hydrochloride (0.5 mole). The pH of this solution was adjusted to between 9.4 and 9.6 with 50 percent aqueous sodium hydroxide solution while the temperature was kept below 50° C. Five hundred twenty-one and three tenths grams of a 63.5 percent solution of the compound of Example 9 was added and the stirred mixture was refluxed for two hours. The product obtained was tested without purification.

EXAMPLE 11

Reaction of 2-Dimethylamino-N,N-bis(phosphonomethyl)ethylamine with Epichlorohydrin Into a 1-liter, four-neck, round-bottom flask equipped with a mechanical stirrer, thermometer, reflux condenser and a dropping funnel was weighed 174.7 g of a 44.78 percent aqueous solution of Example 7 followed by enough 50 pecent aqueous sodium hydroxide to adjust the pH of the mixture to 7.5–7.6. The temperature was raised to 50°–60° C. and 23.0 g of epichlorohydrin (0.25 mole) was slowly introduced. Finally, the mixture was heated at the reflux temperature for two hours. The resulting solution was tested without any further purification or isolation.

EXAMPLE 12

Calcium Carbonate Antiprecipitation Tests

To evaluate the effect of the compounds of the present invention on the precipitation of calcium carbonate, measured volume of stock solution (prepared with demineralized water) of the phosphonic acids or their reaction product with epichlorohydrin were added to 100-ml portions of a calcium hydroxide solution (0.40 g $Ca(OH)_2$ per liter). Then 100 ml of a sodium bicarbonate solution (0.50 g $NaHCO_3$ per liter) was added to each portion of calcium hydroxide solution. The pH of each portion was adjusted to 9.00 (±0.05). The test solutions were then agitated on a rotary shaker for approximately 18 hours at a temperature of 25° C. At the end of this time insoluble material was removed by filtration with Whatman No. 4 filter paper and the calcium ion concentration in the filtrate was determined by titration with a standard ethylenediamine tetraacetic acid solution. The percent inhibition (Table 1) was calculated by comparing the test solution values with two controls included in every test series. The compounds tested were as follows:

A. The reaction product of Example 1.
B. The reaction product of Example 2.
C. The reaction product of Example 3.
D. The reaction product of Example 5.
E. The reaction product of Example 6.
F. The reaction product of Example 7.
G. The reaction product of Example 8.
H. The reaction product of Example 10.
I. The reaction product of Example 11.

EXAMPLE 13

Corrosion Inhibiting Properties of the Compounds of this Invention

This example illustrates the corrosion-inhibiting properties of the compounds of the present invention.

The test apparatus included a sump, a flow circuit, a circulating pump and a heater. The heat coupons were 1010 mild steel. The test fluid was Memphis tap water with the pH adjusted to 7.5 and the temperature was maintained at 50° C.±2° C.

The test fluid containing various concentrations of the compositions described herein was circulated continuously through the system containing the test coupons for a period of three days. At the end of this period, the coupons were removed, cleaned and weighed. The corrosion rates were calculated in milligrams per square decimeter per day (MDD).

The compounds tested are those described in Example 12 from A through I.

TABLE 1.

| Concentration Parts per Million | \multicolumn{9}{c}{Inhibition of Calcium Carbonate Precipitation at pH 9.} |
|---|---|---|---|---|---|---|---|---|---|
| | \multicolumn{9}{c}{PRODUCT TESTED} |
| | A | B | C | D | E | F | G | H | I |
| | \multicolumn{9}{c}{PERCENT INHIBITION} |
| 1.0 | 0 | 16.9 | 0 | 31.0 | 5.9 | 6.2 | 5.6 | 32.7 | 20.4 |
| 2.0 | 0 | 47.4 | 0 | 32.1 | 9.0 | 17.8 | 16.8 | 23.0 | 28.9 |
| 3.0 | 4.2 | 70.4 | 2.0 | 67.9 | 20.7 | 32.3 | 21.2 | 27.0 | 44.3 |
| 4.0 | 41.6 | 76.0 | 11.3 | 82.4 | 28.5 | 35.3 | 31.3 | 33.4 | — |
| 5.0 | 50.9 | 82.4 | 47.1 | 87.2 | 30.1 | 49.5 | 28.0 | 44.4 | 26.4 |
| 6.0 | 54.5 | 90.2 | 0 | 88.3 | 41.0 | 55.6 | 34.0 | 48.8 | 22.1 |
| 7.0 | 64.1 | 90.5 | 4.5 | 93.1 | 50.4 | 65.2 | 33.2 | 50.4 | 57.0 |
| 8.0 | 60.6 | 92.9 | 25.6 | 94.8 | 52.0 | 69.6 | 35.3 | 56.8 | 82.1 |
| 9.0 | 69.4 | 93.2 | 28.7 | 95.9 | 57.4 | 77.7 | 47.9 | 52.5 | 77.0 |
| 10.0 | 67.5 | 93.6 | 36.9 | 92.4 | 60.0 | 78.6 | 43.8 | 55.4 | 87.7 |
| Control | 2.05 | 2.05 | 1.21 | 1.45 | 1.21 | 0.71 | 0.89 | 0.89 | 2.98 |
| $Ca^{++}$ blank | 6.14 | 6.14 | 6.09 | 4.35 | 6.09 | 6.00 | 5.71 | 5.71 | 5.33 |

TABLE 2.

| | \multicolumn{7}{c}{Corrosion Inhibition with the Compounds of this Invention} |
| Corrosion Inhibitor | Concentration Parts per Million | Initial pH | Final pH | \multicolumn{4}{c}{CORROSION RATE} | Inhibition Percent |
| | | | | Sump 1 | Sump 2 | Copper Couple | Average | |
| | | | | \multicolumn{4}{c}{Miligrams per decimeter per day} | |
| A | 50 | 7.5 | 7.2 | 1.33 | 0.18 | 3.01 | 1.51 | 99.4 |
| | 100 | 7.5 | 7.5 | 0.89 | 1.77 | 1.06 | 1.24 | 99.5 |
| | 200 | 7.5 | 7.7 | 1.15 | 1.33 | 3.90 | 2.13 | 99.2 |
| B | 50 | 7.5 | 7.8 | 0.35 | 0.18 | 0.98 | 0.50 | 99.8 |
| | 100 | 7.5 | 7.9 | 0.53 | 0.62 | 1.24 | 0.80 | 99.7 |
| | 200 | 7.5 | 7.9 | 0.62 | 0.09 | 1.86 | 0.86 | 99.7 |
| C | 50 | 7.5 | 8.1 | 8.51 | 5.85 | 5.59 | 6.65 | 97.5 |
| | 100 | 7.5 | 8.2 | 4.61 | 3.46 | 4.43 | 4.17 | 98.4 |
| | 150 | 7.5 | 8.1 | 5.41 | 6.38 | 7.27 | 6.35 | 97.6 |
| D | 50 | 7.5 | 8.3 | 2.04 | 3.01 | 2.04 | 2.36 | 99.1 |
| | 100 | 7.5 | 8.2 | 1.42 | 1.15 | 4.08 | 2.22 | 99.2 |
| | 150 | 7.5 | 8.1 | 2.66 | 2.57 | 6.03 | 3.75 | 98.6 |
| E | 50 | 7.5 | 7.6 | 12.06 | 15.87 | 4.34 | 10.76 | 95.9 |
| | 100 | 7.5 | 7.9 | 3.19 | 2.48 | 3.37 | 3.01 | 98.9 |
| | 150 | 7.5 | 7.9 | 3.46 | 3.90 | 5.05 | 4.14 | 98.4 |
| F | 50 | 7.5 | 8.0 | 12.94 | 53.37 | 40.08 | 35.46 | 86.6 |
| | 100 | 7.5 | 7.9 | 1.24 | 1.51 | 1.95 | 1.57 | 99.4 |
| | 150 | 7.5 | 7.9 | 1.15 | 1.06 | 0.98 | 1.06 | 99.6 |
| G | 50 | 7.5 | 8.1 | 58.60 | 33.51 | 80.14 | 57.42 | 78.3 |

TABLE 2.-continued

| Corrosion Inhibitor | Concentration Parts per Million | Initial pH | Final pH | CORROSION RATE Sump 1 | Sump 2 | Copper Couple | Average | Inhibition Percent |
|---|---|---|---|---|---|---|---|---|
| | | | | Miligrams per decimeter per day | | | | |
| | 100 | 7.5 | 8.0 | 8.69 | 8.78 | 22.43 | 13.30 | 95.0 |
| | 150 | 7.5 | 8.0 | 72.43 | 81.83 | 134.31 | 96.19 | 63.7 |
| H | 50 | 7.5 | 7.5 | 4.00 | 5.05 | 6.12 | 5.06 | 98.1 |
| | 100 | 7.5 | 8.0 | 6.21 | 4.96 | 5.41 | 5.53 | 97.9 |
| | 150 | 7.5 | 8.0 | 3.37 | 6.03 | 17.82 | 9.07 | 96.6 |
| I | 50 | 7.5 | 8.4 | 2.30 | 3.81 | 2.66 | 2.92 | 98.9 |
| | 100 | 7.5 | 8.1 | 1.95 | 2.30 | 3.99 | 2.75 | 99.0 |
| | 150 | 7.5 | 8.0 | 2.04 | 2.04 | 5.38 | 3.15 | 98.8 |
| Control | 0 | 7.5 | 7.8 | 193.0 | 258.0 | 356.0 | 269.0 | 0 |

Water: Memphis Tap Water
Temperature: 50° C.
Time: Three days

EXAMPLE 14

Reaction of 3-(N,N-Dimethylamino)-N',N'-bis(phosphonomethyl)-propylamine with Epichlorohydrin A solution was prepared by mixing 1170 g (10.0 moles) of phosphorous acid (70 percent in water) and 806 g (8.4 moles) of hydrochloric acid (38 percent in water). To this solution was added 408 g (4.0 moles) of 3-dimethylaminopropylamine while cooling. The reaction mixture was then heated to 110°–115° C. and 681 g (8.4 moles) of formaldehyde (37 percent in water) was added dropwise. The mixture was then heated at reflux for three hours and excess reagents were removed at the end of the heating cycle by distilling 533 g from the mixture.

An aliquot, which weighed 1266 g, was treated with 989 g of 50 percent sodium hydroxide solution to a pH of 10.5 while the temperature was kept below 40° C. The mixture was cloudy and viscous so 200 g of water was added to obtain a clear solution.

One-tenth of a mole of the trisodium salt of 3-(N,N-dimethylamino)-N',-bis(phosphonomethyl)propylamine was contained in 122.1 g of the above solution. This amount was mixed with 4.8 g (0.05 mole) of hydrochloric acid (38 percent in water) and 4.6 g (0.05 mole) of epichlorohydrin. The mixture was agitated at room temperature for sixteen hours and then refluxed for two hours. A clear solution was obtained.

The product obtained was tested as a calcium carbonate antiprecipitant using the method described in Example 12 except that the pH was not adjusted to pH 9. At 3 parts per million, 85 percent inhibition of precipitation was obtained.

While particular embodiments of the invention have been described, it will be understood, of course, that the invention is not limited thereto since many modifications may be made, and it is, therefore, contemplated to cover by the appended claims any such modifications as fall within the true spirit and scope of the invention.

The invention having thus been described, what is claimed and desired to be secured by Letters Patent is:

1. As a new composition of matter a compound having the formula

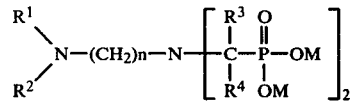

wherein $R^1$ and $R^2$ represent an alkyl group containing 1 to 4 carbon atoms, $R^3$ and $R^4$ represent hydrogen or an alkyl group containing 1 to 4 carbon atoms, M represents hydrogen, alkali metal or ammonium, and n is an integer varying from 2 to 6 and the hydrochloride salts thereof.

2. The compound according to claim 1 identified as 2-(N,N-dimethylamino)-N',N'-bis(phosphonomethyl)ethylamine hydrochloride.

3. The compound according to claim 1 wherein M is an alkali metal.

4. The compound according to claim 1 wherein M is $NH_4$.

5. The compound according to claim 1 identified as 3-(N,N-dimethylamino)-N',N'-bis(phosphonomethyl)-propylamine hydrochloride.

* * * * *